US011013425B2

(12) United States Patent
Fonte et al.

(10) Patent No.: US 11,013,425 B2
(45) Date of Patent: May 25, 2021

(54) SYSTEMS AND METHODS FOR ANALYZING AND PROCESSING DIGITAL IMAGES TO ESTIMATE VESSEL CHARACTERISTICS (71) Applicant: HeartFlow, Inc., Redwood City, CA (US)

(72) Inventors: Timothy A. Fonte, San Francisco, CA (US); Gilwoo Choi, Mountain View, CA (US); Leo Grady, New York, NY (US); Michael Singer, Belmont, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 16/944,772

(22) Filed: Jul. 31, 2020

(65) Prior Publication Data

US 2020/0359910 A1   Nov. 19, 2020

Related U.S. Application Data

(63) Continuation of application No. 15/961,449, filed on Apr. 24, 2018, which is a continuation of application
(Continued)

(51) Int. Cl.
*G06K 9/00* (2006.01)
*A61B 5/026* (2006.01)
(Continued)

(52) U.S. Cl.
CPC ............ *A61B 5/026* (2013.01); *A61B 5/0022* (2013.01); *A61B 5/021* (2013.01); *A61B 5/0205* (2013.01);
(Continued)

(58) Field of Classification Search
CPC ... A61B 5/026; A61B 5/0022; A61B 5/02007; A61B 5/0205; A61B 5/021; A61B 5/107;
(Continued)

(56) References Cited

U.S. PATENT DOCUMENTS 5,533,511 A   7/1996   Kaspari et al.
6,377,832 B1   4/2002   Bergman et al.
(Continued)

FOREIGN PATENT DOCUMENTS

JP   H01145043 A   6/1989
JP   H0824227 A    1/1996
(Continued)

OTHER PUBLICATIONS

Bernhard, Stefan et al., "Transient integral boundary layer method to calculate the translesional pressure drop and the fractional flow reserve in myocardial bridges," Biomedical Engineering Online, Biomed Central Ltd., London, GB, vol. 5, No. 1, Jun. 21, 2006, p. 42.
(Continued)

*Primary Examiner* — Jonathan S Lee
(74) *Attorney, Agent, or Firm* — Bookoff McAndrews, PLLC (57) ABSTRACT

Systems and methods are disclosed for determining individual-specific blood flow characteristics. One method includes acquiring, for each of a plurality of individuals, individual-specific anatomic data and blood flow characteristics of at least part of the individual's vascular system; executing a machine learning algorithm on the individual-specific anatomic data and blood flow characteristics for each of the plurality of individuals; relating, based on the executed machine learning algorithm, each individual's individual-specific anatomic data to functional estimates of blood flow characteristics; acquiring, for an individual and
(Continued)

individual-specific anatomic data of at least part of the individual's vascular system; and for at least one point in the individual's individual-specific anatomic data, determining a blood flow characteristic of the individual, using relations from the step of relating individual-specific anatomic data to functional estimates of blood flow characteristics.

20 Claims, 2 Drawing Sheets

Related U.S. Application Data

No. 15/200,402, filed on Jul. 1, 2016, now Pat. No. 9,974,453, which is a continuation of application No. 13/895,871, filed on May 16, 2013, now Pat. No. 10,433,740.

(60) Provisional application No. 61/793,673, filed on Mar. 15, 2013, provisional application No. 61/700,213, filed on Sep. 12, 2012.

(51) Int. Cl.
*G06N 20/00* (2019.01)
*A61B 6/00* (2006.01)
*G16H 50/20* (2018.01)
*A61B 5/02* (2006.01)
*A61B 5/0205* (2006.01)
*A61B 5/021* (2006.01)
*A61B 5/107* (2006.01)
*A61B 5/00* (2006.01)
*A61B 6/03* (2006.01)
*A61B 5/145* (2006.01)
*G06N 7/00* (2006.01)
*A61B 5/024* (2006.01)

(52) U.S. Cl.
CPC .......... *A61B 5/02007* (2013.01); *A61B 5/107* (2013.01); *A61B 5/14535* (2013.01); *A61B 5/14546* (2013.01); *A61B 5/7267* (2013.01); *A61B 5/7278* (2013.01); *A61B 5/7282* (2013.01); *A61B 5/742* (2013.01); *A61B 5/743* (2013.01); *A61B 6/032* (2013.01); *A61B 6/463* (2013.01); *A61B 6/504* (2013.01); *A61B 6/507* (2013.01); *A61B 6/5217* (2013.01); *A61B 6/563* (2013.01); *G06N 7/005* (2013.01); *G06N 20/00* (2019.01); *G16H 50/20* (2018.01); *A61B 5/024* (2013.01); *A61B 2560/0475* (2013.01)

(58) Field of Classification Search
CPC ............ A61B 5/14535; A61B 5/14546; A61B 5/7267; A61B 5/7278; A61B 5/7282; A61B 5/742; A61B 5/743; A61B 6/032; A61B 6/463; A61B 6/504; A61B 6/507; A61B 6/5217; A61B 6/563; A61B 5/024; A61B 2560/0475; G06F 19/345; G06N 7/005; G06N 99/005
USPC ...................................................... 382/128
See application file for complete search history.

(56) References Cited

U.S. PATENT DOCUMENTS

| | | | |
|---|---|---|---|
| 8,098,918 | B2 | 1/2012 | Zheng et al. |
| 8,315,812 | B2 | 11/2012 | Taylor |
| 8,684,921 | B2 | 4/2014 | Osorio |
| 8,821,408 | B2 | 9/2014 | Hu et al. |
| 9,349,178 | B1 | 5/2016 | Itu et al. |
| 2003/0004652 | A1 | 1/2003 | Brunner et al. |
| 2003/0087244 | A1 | 5/2003 | McCarthy |
| 2005/0059876 | A1 | 3/2005 | Krishnan et al. |
| 2008/0292049 | A1 | 11/2008 | Camus et al. |
| 2009/0080745 | A1 | 3/2009 | Zheng et al. |
| 2009/0103794 | A1 | 4/2009 | Sathyanarayana |
| 2011/0060576 | A1 | 3/2011 | Sharma et al. |
| 2011/0071404 | A1 | 3/2011 | Schmitt et al. |
| 2011/0282169 | A1 | 11/2011 | Grudic et al. |
| 2012/0022843 | A1 | 1/2012 | Ionasec et al. |
| 2012/0041318 | A1 | 2/2012 | Taylor |
| 2012/0053918 | A1 | 3/2012 | Taylor |
| 2012/0059246 | A1 | 3/2012 | Taylor |
| 2012/0072190 | A1 | 3/2012 | Sharma et al. |
| 2012/0142632 | A1 | 6/2012 | Campbell |
| 2012/0201446 | A1 | 8/2012 | Yang et al. |
| 2012/0232853 | A1 | 9/2012 | Voigt et al. |
| 2013/0132054 | A1 | 5/2013 | Sharma et al. |
| 2013/0197884 | A1 | 8/2013 | Mansi et al. |
| 2013/0243294 | A1 | 9/2013 | Ralovich et al. |
| 2013/0246034 | A1 | 9/2013 | Sharma et al. |
| 2014/0073976 | A1 | 3/2014 | Fonte et al. |
| 2014/0100451 | A1 | 4/2014 | Tolkowsky et al. |
| 2014/0114184 | A1 | 4/2014 | Klaiman et al. |
| 2014/0121513 | A1* | 5/2014 | Tolkowsky ............ A61B 6/481 600/431 |
| 2014/0220580 | A1 | 8/2014 | Brown et al. |
| 2014/0249784 | A1 | 9/2014 | Sankaran et al. |
| 2015/0042646 | A1 | 2/2015 | Comaniciu et al. |
| 2015/0112182 | A1 | 4/2015 | Sharma et al. |
| 2015/0282765 | A1 | 10/2015 | Goshen et al. |
| 2016/0148371 | A1 | 5/2016 | Itu et al. |
| 2016/0148372 | A1 | 5/2016 | Itu et al. |
| 2016/0166209 | A1 | 6/2016 | Itu et al. |
| 2017/0014033 | A1* | 1/2017 | Koo ...................... G16H 50/30 |

FOREIGN PATENT DOCUMENTS

| | | |
|---|---|---|
| JP | H0824227 B2 | 3/1996 |
| JP | 2007526016 A | 9/2007 |
| JP | 2012024582 A | 2/2012 |
| JP | 2012159990 A | 8/2012 |
| JP | 2013534154 A | 9/2013 |
| JP | 2015527901 A | 9/2015 |
| JP | 2016028747 A | 3/2016 |
| JP | 2017512577 A | 5/2017 |
| WO | 2005001769 A2 | 1/2005 |
| WO | 2011015822 A1 | 2/2011 |

OTHER PUBLICATIONS

Deng, Jan. 1, 2012, Three Classes of Deep Learning Architectures and Their Applications: A Tutorial Survey, APSIPA Transactions on Signal and Information Processing.
English-language translation of Notice of Preliminary Rejection dated Aug. 11, 2015, in corresponding Korean Patent Application No. 10-2015-7006740, filed on Aug. 30, 2013 (4 pages).
English-language translation of Notice of Reasons for Rejection dated Sep. 9, 2015, in corresponding Japanese Patent Application No. 2015-531136, filed on Aug. 30, 2013 (6 pages).
Examination Report pursuant to Article 94(3) EPC dated Nov. 14, 2014 in corresponding European Patent Application No. 13 756 800.2, filed on Aug. 30, 2013 (6 pages).
Filipovic N et al.; "Hemodynamic Flow Modeling Through an Abdominal Aorta Aneurysm Using Data Mining Tools", IEEE Transactions on Information Technology in Biomedicine, vol. 15, No. 2, Mar. 1, 2011, pp. 189-194.
International Preliminary Report on Patentability dated Mar. 26, 2015, in corresponding PCT Application No. PCT/US2013/057546, filed on Aug. 30, 2013 (6 pages).
International Search Report dated Nov. 18, 2013 in corresponding International Application No. PCT/US2013/057546.
Ionasec, Razvan Ioan; Dissertation; "Patient-specific Modeling and Quantification of the Heart Valves from Multimodal Cardiac Images"; Siemens Corporate Research, Jun. 30, 2010. (Technische Universität München).

(56) References Cited

OTHER PUBLICATIONS

Japanese Office Action dated Dec. 5, 2018 in corresponding Japanese Application No. 2018-11463 and English Translation (7 pages).
Krizhevesky et al. 2012, ImageNet Classification with Deep Convolution Neural Networks, Conference: Advances in Neural Information Processing Systems 25, p. 1-9.
Mihalef, Viorel, et al. "Patient-specific modelling of whole heart anatomy, dynamics and haemodynamics from four-dimensional cardiac CT images." Interface Focus 1.3 (2011): 286-296.
Office Action dated Jun. 25, 2015, in corresponding Canadian Patent Application No. 2882543, filed on Aug. 30, 2013 (6 pages).
Office Action dated Mar. 3, 2015, in corresponding Canadian Patent Application No. 2882543, filed on Aug. 30, 2013 (5 pages).
Office Action dated Oct. 8, 2015, in corresponding Canadian Patent Application No. 2882543, filed on Aug. 30, 2013 (3 pages).
Patent Examination Report dated Mar. 18, 2015, in corresponding Australian Patent Application No. 2013315960, filed on Aug. 30, 2013 (3 pages).
Zhou et al., Shape Regression Machine, N. Karssemeijer and B. Lelieveldt (Eds.): IPMI 2007, LNCS 4584, pp. 13-25, 2007, Springer-Verlag Berlin Heidelberg, 200.

* cited by examiner

SYSTEMS AND METHODS FOR ANALYZING AND PROCESSING DIGITAL IMAGES TO ESTIMATE VESSEL CHARACTERISTICS

RELATED APPLICATION

This application is a continuation of U.S. application Ser. No. 15/961,449, filed on Apr. 24, 2018, which is a continuation of U.S. application Ser. No. 15/200,402, filed on Jul. 1, 2016, now U.S. Pat. No. 9,974,453, which is a continuation of U.S. application Ser. No. 13/895,871, filed on May 16, 2013, now U.S. Pat. No. 10,433,740, which claims priority to U.S. Provisional Application Nos. 61/700,213 filed Sep. 12, 2012, and 61/793,673, filed Mar. 15, 2013, the entire disclosures of which are hereby incorporated by reference in their entireties.

FIELD OF THE INVENTION

Various embodiments of the present disclosure relate generally to medical imaging and related methods. More specifically, particular embodiments of the present disclosure relate to systems and methods for estimating patient-specific blood flow characteristics from vessel geometry and physiology.

In addition, embodiments of the present disclosure relate to rapid estimation of ischemia, blood flow, fractional flow reserve (FFR), or other metrics derived from patient-specific anatomy and characteristics to aid physicians in the diagnosis, management, and treatment of cardiovascular diseases.

BACKGROUND

Cardiovascular diseases are the leading cause of death in the industrialized world and contribute to roughly a third of global deaths. The predominant form of acquired cardiovascular disease, atherosclerosis, results from the chronic buildup of fatty material in the inner layer of the arteries supplying the heart, brain, kidneys, digestive system, and lower extremities. Progressive coronary artery disease restricts blood flow to the heart, presenting as chest pain during physical exertion, referred to as chronic stable angina, or when the patient is at rest, known as unstable angina. More severe manifestation of disease may lead to myocardial infarction, or heart attack. Patients presenting with chest pain are usually subject to a range of currently available noninvasive tests, including ECG, treadmill tests, SPECT, PET, and CT—none of which measure blood flow and provide only anatomic information or indirect indications of disease. Due to the lack of accurate functional information provided by current noninvasive tests, many patients require invasive catheter procedures to assess coronary blood flow. There is a pressing need for a noninvasive means to quantify blood flow in the human coronary arteries to assess the functional significance of diffuse and focal coronary artery disease. Additionally, there is a need to achieve rapid assessment of blood flow to enable use in emergency rooms, in-patient treatment, and onsite hospital use. In addition to non-invasive use, there is a need within invasive imaging, such as coronary angiography, to quickly estimate functional metrics without the need for pressure or flow wires or special medication. Such a technology is also applicable to preventing, diagnosing, managing and treating disease in other portions of the cardiovascular system including the arteries of the neck, e.g. the carotid arteries, the arteries in the head, e.g. the cerebral arteries, the arteries in the abdomen, e.g. the abdominal aorta and its branches, the arteries in legs, e.g. the femoral and popliteal arteries.

A functional assessment of arterial capacity is important for treatment planning to address patient needs. Recent studies have demonstrated that hemodynamic characteristics, such as Fractional Flow Reserve (FFR), are important indicators to determine the optimal treatment for a patient with arterial disease. Conventional assessments of these hemodynamic characteristics use invasive catheterizations to directly measure blood flow characteristics, such as pressure and flow velocity. However, despite the important clinical information that is gathered, these invasive measurement techniques present severe risks to the patient and significant costs to the healthcare system.

To address the risks and costs associated with invasive measurement, a new generation of noninvasive tests have been developed to assess blood flow characteristics. These noninvasive tests use patient imaging (such as computed tomography (CT)) to determine a patient-specific geometric model of the blood vessels and this model is used computationally to simulate the blood flow using computational fluid dynamics (CFD) with appropriate physiological boundary conditions and parameters. Examples of inputs to these patient-specific boundary conditions include the patient's blood pressure, blood viscosity and the expected demand of blood from the supplied tissue (derived from scaling laws and a mass estimation of the supplied tissue from the patient imaging). Although these simulation-based estimations of blood flow characteristics have demonstrated a level of fidelity comparable to direct (invasive) measurements of the same quantity of interest, physical simulations demand a substantial computational burden that can make these virtual, noninvasive tests difficult to execute in a real-time clinical environment. Consequently, the present disclosure describes new approaches for performing rapid, noninvasive estimations of blood flow characteristics that are computationally inexpensive.

SUMMARY

Systems and methods are disclosed for deriving a patient-specific geometric model of a patient's blood vessels, and combining this geometry with the patient-specific physiological information and boundary conditions. Combined, these data may be used to estimate the patient's blood flow characteristics and predict clinically relevant quantities of interest (e.g., FFR). The presently disclosed systems and methods offer advantages over physics-based simulation of blood flow to compute the quantity of interest, such as by instead using machine learning to predict the results of a physics-based simulation. In one embodiment, disclosed systems and methods involve two phases: first, a training phase in which a machine learning system is trained to predict one or more blood flow characteristics; and second, a production phase in which the machine learning system is used to produce one or more blood flow characteristics and clinically relevant quantities of interest. In the case of predicting multiple blood flow characteristics, this machine learning system can be applied for each blood flow characteristic and quantity of interest.

According to one embodiment, a method is disclosed for determining individual-specific blood flow characteristics. The method includes acquiring, for each of a plurality of individuals, individual-specific anatomic data and blood flow characteristics of at least part of the individual's vascular system; executing a machine learning algorithm on the individual-specific anatomic data and blood flow characteristics for each of the plurality of individuals; relating, based on the executed machine learning algorithm, each individual's individual-specific anatomic data to functional estimates of blood flow characteristics; acquiring, for an individual, individual-specific anatomic data of at least part of the individual's vascular system; and for at least one point in the individual's individual-specific anatomic data, determining a blood flow characteristic of the individual, using relations from the step of relating individual-specific anatomic data to functional estimates of blood flow characteristics.

According to one embodiment, a system is disclosed for determining individual-specific blood flow characteristics. The system includes a data storage device storing instructions for estimating individual-specific blood flow characteristics; and a processor configured to execute the instructions to perform a method including the steps of: acquiring, for each of a plurality of individuals, individual-specific anatomic data and blood flow characteristics of at least part of the individual's vascular system; executing a machine learning algorithm on the individual-specific anatomic data and blood flow characteristics for each of the plurality of individuals; relating, based on the executed machine learning algorithm, each individual's individual-specific anatomic data to functional estimates of blood flow characteristics; acquiring, for an individual, individual-specific anatomic data of at least part of the individual's vascular system; and for at least one point in the individual's individual-specific anatomic data, determining a blood flow characteristic of the individual, using relations from the step of relating individual-specific anatomic data to functional estimates of blood flow characteristics.

According to one embodiment, a non-transitory computer-readable medium storing instructions that, when executed by a computer, cause the computer to perform a method including: acquiring, for each of a plurality of individuals, individual-specific anatomic data and blood flow characteristics of at least part of the individual's vascular system; executing a machine learning algorithm on the individual-specific anatomic data and blood flow characteristics for each of the plurality of individuals; relating, based on the executed machine learning algorithm, each individual's individual-specific anatomic data to functional estimates of blood flow characteristics; acquiring, for an individual, individual-specific anatomic data of at least part of the individual's vascular system; and for at least one point in the individual's individual-specific anatomic data, determining a blood flow characteristic of the individual, using relations from the step of relating individual-specific anatomic data to functional estimates of blood flow characteristics.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

The present disclosure describes certain principles and embodiments for providing advantages over physics-based simulation of blood flow to compute patient-specific blood flow characteristics and clinically relevant quantities of interest. Namely, the presently disclosed systems and methods may incorporate machine learning techniques to predict the results of a physics-based simulation. For example, the present disclosure describes an exemplary, less processing-intensive technique, which may involve modeling the fractional flow reserve (FFR) as a function of a patient's vascular cross-sectional area, diseased length, and boundary conditions. The cross-sectional area may be calculated based on lumen segment and plaque segment, among other things. The diseased length may be calculated based on plaque segment and stenosis location, among other things. The boundary conditions may reflect patient-specific physiology, such as coronary flow (estimated from myocardial mass), outlet area, and hyperemic assumptions, to reflect that different patients have different geometry and physiologic responses.

In one embodiment, fractional flow reserve may be modeled as a function of a patient's boundary conditions (f(BCs)), and a function of a patient's vascular geometry (g(areaReductions)). Although the patient's geometry may be described as a function of "areaReductions," it should be appreciated that this term refers, not just to changes in patient's vascular cross-sectional area, but to any physical or geometric characteristics affecting a patient's blood flow. In one embodiment, FFR can be predicted by optimizing the functions "f" and "g" such that the difference between the estimated FFR ($FFR_{CT\_ScalingLaw}$) and the measured FFR (mFFR) is minimized. In other words, machine learning techniques can be used to solve for the functions that cause the estimated FFR to approximate the measured FFR. In one embodiment, the measured FFR may be calculated by traditional catheterized methods or by modern, computational fluid dynamics (CFD) techniques. In one embodiment, one or more machine learning algorithms may be used to optimize the functions of boundary conditions and patient geometry for hundreds or even thousands of patients, such that estimates for FFR can reliably approximate measured FFR values. Thus, FFR values calculated by CFD techniques can be valuable for training the machine learning algorithms.

Figure 1:
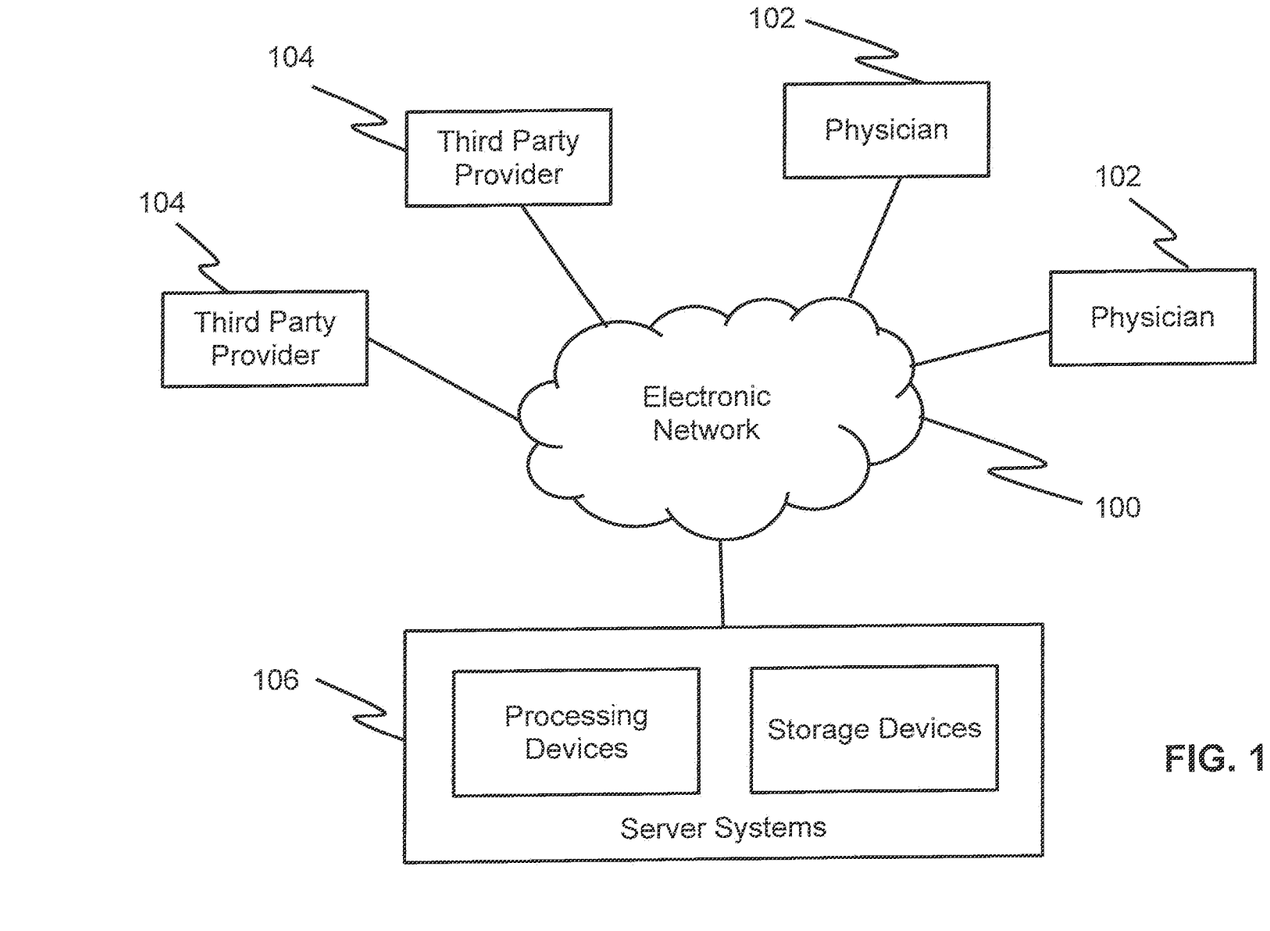
FIG. 1 is a block diagram of an exemplary system and network for estimating patient-specific blood flow characteristics from vessel geometry and physiological information, according to an exemplary embodiment of the present disclosure.

Referring now to the figures, FIG. 1 depicts a block diagram of an exemplary system and network for estimating patient-specific blood flow characteristics from vessel geometry and physiological information. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Sever systems 106 may also include processing devices for processing images and data stored in the storage devices.

Figure 2:
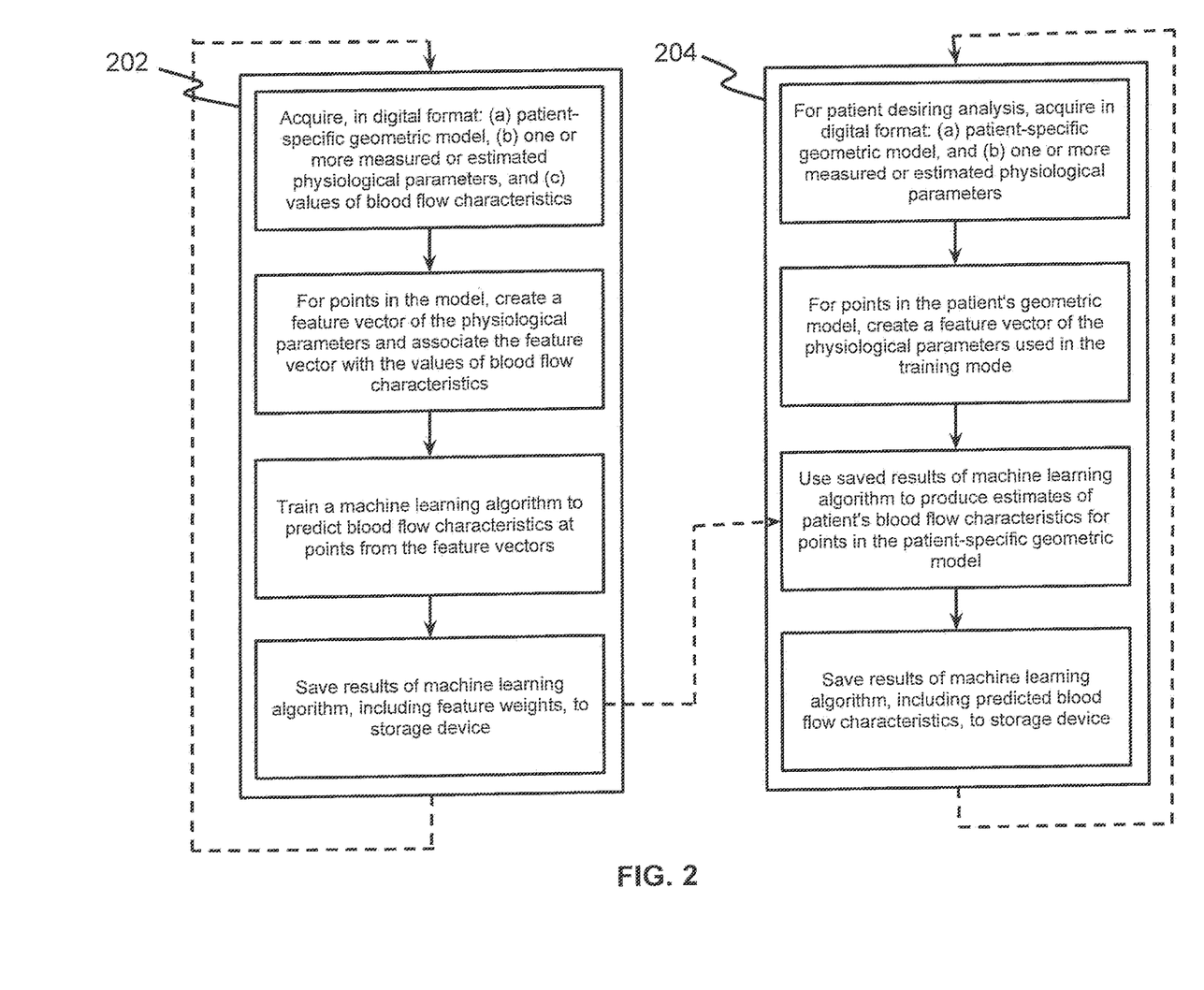
FIG. 2 is a block diagram of an exemplary method for estimating patient-specific blood flow characteristics from vessel geometry and physiological information, according to an exemplary embodiment of the present disclosure.

FIG. 2 is a block diagram of an exemplary method for estimating patient-specific blood flow characteristics from vessel geometry and physiological information, according to an exemplary embodiment of the present disclosure. The method of FIG. 2 may be performed by server systems 106, based on information received from physicians 102 and/or third party providers 104 over electronic network 100.

In one embodiment, the method of FIG. 2 may include a training method 202, for training one or more machine learning algorithms based on numerous patients' blood flow characteristic estimates, and a production method 204 for using the machine learning algorithm results to predict a particular patient's blood flow characteristics.

In one embodiment, training method 202 may be performed based on FFR estimates generating using CFD techniques for hundreds of patients. Training method 202 may involve acquiring, for each of a plurality of individuals, e.g., in digital format: (a) a patient-specific geometric model, (b) one or more measured or estimated physiological parameters, and (c) values of blood flow characteristics. Training method 202 may then involve, for one or more points in each patient's model, creating a feature vector of the patients' physiological parameters and associating the feature vector with the values of blood flow characteristics. For example, training method 202 may associate an estimated FFR with every point in a patient's geometric model. Training method 202 may then train a machine learning algorithm (e.g., using processing devices of server systems 106) to predict blood flow characteristics at each point of a geometric model, based on the feature vectors and blood flow characteristics. Training method 202 may then save the results of the machine learning algorithm, including feature weights, in a storage device of server systems 106. The stored feature weights may define the extent to which patient features or geometry are predictive of certain blood flow characteristics.

In one embodiment, the production method 204 may involve estimating FFR values for a particular patient, based on results of executing training method 202. In one embodiment, production method 204 may include acquiring, e.g. in digital format: (a) a patient-specific geometric model, and (b) one or more measured or estimated physiological parameters. For multiple points in the patient's geometric model, production method 204 may involve creating a feature vector of the physiological parameters used in the training mode. Production method 204 may then use saved results of the machine learning algorithm to produce estimates of the patient's blood flow characteristics for each point in the patient-specific geometric model. Finally, production method 204 may include saving the results of the machine learning algorithm, including predicted blood flow characteristics, to a storage device of server systems 106.

Described below are general and specific exemplary embodiments for implementing a training mode and a production mode of machine learning for predicting patient-specific blood flow characteristics, e.g. using server systems 106 based on images and data received from physicians 102 and/or third party providers 104 over electronic network 100.

General Embodiment

In a general embodiment, server systems 106 may perform a training mode based on images and data received from physicians 102 and/or third party providers 104 over electronic network 100. Specifically, for one or more patients, server systems 106 may acquire a digital representation (e.g., the memory or digital storage [e.g., hard drive, network drive] of a computational device such as a computer, laptop, DSP, server, etc.) of the following items: (a) a patient-specific model of the geometry for one or more of the patient's blood vessels; (b) a list of one or more measured or estimated physiological or phenotypic parameters of the patient; and/or (c) measurements, estimations or simulated values of all blood flow characteristic being targeted for prediction. In one embodiment, the patient-specific model of the geometry may be represented by a list of points in space (possibly with a list of neighbors for each point) in which the space can be mapped to spatial units between points (e.g., millimeters). In one embodiment, the list of one or more measured or estimated physiological or phenotypic parameters of the patient may include blood pressure, blood viscosity, patient age, patient gender, mass of the supplied tissue, etc. These patient-specific parameters may be global (e.g., blood pressure) or local (e.g., estimated density of the vessel wall at a particular location).

For every point in the patient-specific geometric model for which there is a measured, estimated or simulated value of the blood flow characteristic, server systems 106 may then create a feature vector for that point. The feature vector may be a numerical description of the patient-specific geometry at that point and estimates of physiological or phenotypic parameters of the patient. The feature vector may contain both global and local physiological or phenotypic parameters, where: for global parameters, all points have the same numerical value; and for local parameters, the value(s) may change at different points in the feature vector. Server systems 106 may then associate this feature vector with the measured, estimated or simulated value of the blood flow characteristic at this point.

Server systems 106 may then train a machine learning algorithm to predict the blood flow characteristics at the points from the feature vectors at the points. Examples of machine learning algorithms that can perform this task are support vector machines (SVMs), multi-layer perceptrons (MLPs), and multivariate regression (MVR) (e.g., weighted linear or logistic regression). Server systems 106 may then save the results of the machine learning algorithm (e.g., feature weights) to a digital representation (e.g., the memory or digital storage [e.g., hard drive, network drive] of a computational device such as a computer, laptop, DSP, server, etc.).

Also in a general embodiment, server systems 106 may perform a production mode based on images and data received from physicians 102 and/or third party providers 104 over electronic network 100. For a patient on whom a blood flow analysis is to be performed, server systems 106 may acquire a digital representation (e.g., the memory or digital storage [e.g., hard drive, network drive] of a computational device such as a computer, laptop, DSP, server, etc.) of (a) a patient-specific model of the geometry for one or more of the patient's blood vessels; and (b) a list of one or more estimates of physiological or phenotypic parameters of the patient. In one embodiment, the patient-specific model of the geometry for one or more of the patient's blood vessels may be represented as a list of points in space (possibly with a list of neighbors for each point) in which the space can be mapped to spatial units between points (e.g., millimeters). The list of one or more estimates of physiological or phenotypic parameters of the patient, may include blood pressure, blood viscosity, patient age, patient gender, the mass of the supplied tissue, etc. These parameters may be global (e.g., blood pressure) or local (e.g., estimated density of the vessel wall at a location). This list of parameters must be the same as the list used in the training mode.

For every point in the patient-specific geometric model, server systems 106 may create a feature vector that consists of a numerical description of the geometry and estimates of physiological or phenotypic parameters of the patient. Global physiological or phenotypic parameters can be used in the feature vector of all points and local physiological or phenotypic parameters can change in the feature vector of different points. These feature vectors may represent the same parameters used in the training mode. Server systems 106 may then use the saved results of the machine learning algorithm produced in the training mode (e.g., feature weights) to produce estimates of the blood flow characteristics at each point in the patient-specific geometric model. These estimates may be produced using the same machine learning algorithm technique used in the training mode (e.g., the SVM, MLP, MVR technique). Server systems 106 may also save the predicted blood flow characteristics for each point to a digital representation (e.g., the memory or digital storage [e.g., hard drive, network drive] of a computational device such as a computer, laptop, DSP, server, etc.).

Exemplary Embodiment

In one exemplary embodiment, server systems 106 may perform a training mode based on images and data received from physicians 102 and/or third party providers 104 over electronic network 100. Specifically, for one or more patients, server systems 106 may acquire a digital representation (e.g., the memory or digital storage [e.g., hard drive, network drive] of a computational device such as a computer, laptop, DSP, server, etc.) of (a) a patient-specific model of the geometry for the patient's ascending aorta and coronary artery tree; (b) a list of measured or estimated physiological or phenotypic parameters of the patient; and (c) measurements of the FFR when available.

In one embodiment, the patient-specific model of the geometry for the patient's ascending aorta and coronary artery tree may be represented as a list of points in space (possibly with a list of neighbors for each point) in which the space can be mapped to spatial units between points (e.g., millimeters). This model may be derived by performing a cardiac CT imaging study of the patient during the end diastole phase of the cardiac cycle. The resulting CT images may then be segmented manually or automatically to identify voxels belonging to the aorta and to the lumen of the coronary arteries. Once all relevant voxels are identified, the geometric model can be derived (e.g., using marching cubes).

In one embodiment, the list of measured or estimated physiological or phenotypic parameters of the patient may be obtained and may include: (i) systolic and diastolic blood pressures; (ii) heart rate; (iii) hematocrit level; (iv) patient age, gender, height, weight, general health status (presence or absence of diabetes, current medications); (v) lifestyle characteristics: smoker/non-smoker; and/or (vi) myocardial mass (may be derived by segmenting the myocardium obtained during the CT imaging study and then calculating the volume in the image; the mass is then computed using the computed volume and an estimated density (1.05 g/mL) of the myocardial mass.

In one embodiment, measurements of the FFR may be obtained when available. If the measured FFR value is not available at a given spatial location in the patient-specific geometric model, then a numerically computed value of the FFR at the point may be used. The numerically computed values may be obtained from a previous CFD simulation using the same geometric model and patient-specific boundary conditions derived from the physiological and phenotypic parameters listed above.

For every point in the patient-specific geometric model for which there is a measured, estimated or simulated value of the blood flow characteristics, server systems 106 may create a feature vector for that point that contains a numerical description of physiological or phenotypic parameters of the patient and a description of the local geometry. Specifically the feature vector may contain: (i) systolic and diastolic blood pressures; (ii) heart rate; (iii) blood properties including: plasma, red blood cells (erythrocytes), hematocrit, white blood cells (leukocytes) and platelets (thrombocytes), viscosity, yield stress; (iv) patient age, gender, height, weight, etc.; (v) diseases: presence or absence of diabetes, myocardial infarction, malignant and rheumatic conditions, peripheral vascular conditions, etc.; (vi) lifestyle characteristics: presence or absence of current medications/drugs, smoker/non-smoker; (vii) characteristics of the aortic geometry (Cross-sectional area of the aortic inlet and outlet, Surface area and volume of the aorta, Minimum, maximum, and average cross-sectional area, etc.); (viii) characteristics of the coronary branch geometry; and (ix) one or more feature sets.

In one embodiment, the characteristics of the coronary branch geometry may include: (i) volumes of the aorta upstream/downstream of the coronary branch point; (ii) cross-sectional area of the coronary/aorta bifurcation point, i.e., inlet to the coronary branch; (iii) total number of vessel bifurcations, and the number of upstream/downstream vessel bifurcations; (iv) average, minimum, and maximum upstream/downstream cross-sectional areas; (v) distances (along the vessel centerline) to the centerline point of minimum and maximum upstream/downstream cross-sectional areas; (vi) cross-sectional of and distance (along the vessel centerline) to the nearest upstream/downstream vessel bifurcation; (vii) cross-sectional area of and distance (along the vessel centerline) to the nearest coronary outlet and aortic inlet/outlet; (viii) cross-sectional areas and distances (along the vessel centerline) to the downstream coronary outlets with the smallest/largest cross-sectional areas; (ix) upstream/downstream volumes of the coronary vessels; and (x) upstream/downstream volume fractions of the coronary vessel with a cross-sectional area below a user-specified tolerance.

In one embodiment, a first feature set may define cross-sectional area features, such as a cross-sectional lumen area along the coronary centerline, a powered cross-sectional lumen area, a ratio of lumen cross-sectional area with respect to the main ostia (LM, RCA), a powered ratio of lumen cross-sectional area with respect to the main ostia, a degree of tapering in cross-sectional lumen area along the centerline, locations of stenotic lesions, lengths of stenotic lesions, location and number of lesions corresponding to 50%, 75%, 90% area reduction, distance from stenotic lesion to the main ostia, and/or irregularity (or circularity) of cross-sectional lumen boundary.

In one embodiment, the cross-sectional lumen area along the coronary centerline may be calculated by extracting a centerline from constructed geometry, smoothing the centerline if necessary, and computing cross-sectional area at each centerline point and map it to corresponding surface and volume mesh points. In one embodiment, the powered cross-sectional lumen area can be determined from various source of scaling laws. In one embodiment, the ratio of lumen cross-sectional area with respect to the main ostia (LM, RCA) can be calculated by measuring cross-sectional area at the LM ostium, normalizing cross-sectional area of the left coronary by LM ostium area, measuring cross-sectional area at the RCA ostium, and normalizing cross-sectional area of the right coronary by RCA ostium area. In one embodiment, the powered ratio of lumen cross-sectional area with respect to the main ostia can be determined from various source of scaling laws. In one embodiment, the degree of tapering in cross-sectional lumen area along the centerline can be calculated by sampling centerline points within a certain interval (e.g., twice the diameter of the vessel) and compute a slope of linearly-fitted cross-sectional area. In one embodiment, the location of stenotic lesions can be calculated by detecting minima of cross-sectional area curve, detecting locations where first derivative of area curve is zero and second derivative is positive, and computing distance (parametric arc length of centerline) from the main ostium. In one embodiment, the lengths of stenotic lesions can be calculated by computing the proximal and distal locations from the stenotic lesion, where cross-sectional area is recovered.

In one embodiment, another feature set may include intensity features that define, for example, intensity change along the centerline (slope of linearly-fitted intensity variation). In one embodiment, another feature set may include surface features that define, for example, 3D surface curvature of geometry (Gaussian, maximum, minimum, mean). In one embodiment, another feature set may include volume features that define, for example, a ratio of total coronary volume compared to myocardial volume. In one embodiment, another feature set may include centerline features that define, for example, curvature (bending) of coronary centerline, e.g., by computing Frenet curvature:

$$\kappa = \frac{|p' \times p''|}{|p'|^3},$$

where p is coordinate of centerline or by computing an inverse of the radius of circumscribed circle along the centerline points. Curvature (bending) of coronary centerline may also be calculated based on tortuosity (non-planarity) of coronary centerline, e.g., by computing Frenet torsion:

$$\tau = \frac{(p' \times p'') \cdot p'''}{|p' \times p''|^2},$$

where p is coordinate of centerline

In one embodiment, another feature set may include a SYNTAX scoring feature, including, for example, an existence of aorto ostial lesion, detection of a lesion located at the origin of the coronary from the aorta; and/or dominance (left or right).

In one embodiment, another feature set may include a simplified physics feature, e.g., including a fractional flow reserve value derived from Hagen-Poisseille flow assumption (Resistance~Area$^{-2}$). For example, in one embodiment, server systems 106 may compute the cross-sectional area of the origin (LM ostium or RCA ostium) of the coronary from the aorta ($A_O$) with aortic pressure ($P_O$); compute cross-sectional area of coronary vessel ($A_i$) at each sampled interval ($L_i$); determine the amount of coronary flow in each segment of vessel using resistance boundary condition under hyperemic assumption ($Q_i$); estimate resistance at each sampled location ($R_i$) based on:

$$R_i = \alpha_i \frac{8\mu L_i}{\pi A_i^{\gamma_i}} + \beta_i,$$

where:
Nominal value $\mu$=dynamic viscosity of blood, $\alpha_i$=1.0, $\beta_i$=0, $\gamma_i$=2.0 (Hagen-Poisseille).

Server systems 106 may estimate pressure drop ($\Delta P$) as $\Delta P_i = Q_i R_i$ and compute FFR at each sampled location as $$FFR_i = \frac{P_0 - \sum_{k=1}^{i} \Delta P_k}{P_0}.$$

Locations of cross-sectional area minima or intervals smaller than vessel radius may be used for sampling locations. Server systems 106 may interpolate FFR along the centerline using $FFR_i$, project FFR values to 3D surface mesh node, and vary $\alpha_i$, $\beta_i$, $\gamma_i$ and obtain new sets of FFR estimation as necessary for training, such as by using the feature sets defined above to perturb parameters where $\alpha_i$, $\beta_i$ can be a function of the diseased length, degree of stenosis and tapering ratio to account for tapered vessel; and $Q_i$ can be determined by summing distributed flow of each outlet on the basis of the same scaling law as the resistance boundary condition (outlet resistance$\propto$outlet area$^{-1.35}$). However, a new scaling law and hyperemic assumption can be adopted, and this feature vector may be associated with the measurement or simulated value of the FFR at that point. Server systems 106 may also train a linear SVM to predict the blood flow characteristics at the points from the feature vectors at the points; and save the results of the SVM as a digital representation (e.g., the memory or digital storage [e.g., hard drive, network drive] of a computational device such as a computer, laptop, DSP, server, etc.).

In an exemplary production mode, servers systems 106 may, for a target patient, acquire in digital representation (e.g., the memory or digital storage (e.g., hard drive, network drive) of a computational device such as a computer, laptop, DSP, server, etc.): (a) a patient-specific model of the geometry for the patient's ascending aorta and coronary artery tree; and (b) a list of physiological and phenotypic parameters of the patient obtained during training mode. In one embodiment, the patient-specific model of the geometry for the patient's ascending aorta and coronary artery tree may be represented as a list of points in space (possibly with a list of neighbors for each point) in which the space can be mapped to spatial units between points (e.g., millimeters). This model may be derived by performing a cardiac CT imaging of the patient in the end diastole phase of the cardiac cycle. This image then may be segmented manually or automatically to identify voxels belonging to the aorta and the lumen of the coronary arteries. Once the voxels are identified, the geometric model can be derived (e.g., using marching cubes). The process for generating the patient-specific model of the geometry may be the same as in the training mode. For every point in the patient-specific geometric model, the server systems 106 may create a feature vector for that point that consists of a numerical description of the geometry at that point and estimates of physiological or phenotypic parameters of the patient. These features may be the same as the quantities used in the training mode. The server systems 106 may then use the saved results of the machine learning algorithm produced in the training mode (e.g., feature weights) to produce estimates of the FFR at each point in the patient-specific geometric model. These estimates may be produced using the same linear SVM technique used in the training mode. The server systems 106 may save the predicted FFR values for each point to a digital representation (e.g., the memory or digital storage [e.g., hard drive, network drive] of a computational device such as a computer, laptop, DSP, server, etc.).

In one embodiment, the above factors (i) thru (viii) ("Systolic and diastolic blood pressures" thru "Characteristics of the coronary branch geometry") may be considered global features, which are applicable to all points within a given patient's geometric model. Also, items (ix) thru (xv) ("Feature Set I: Cross-sectional area feature" thru "Feature Set VII: Simplified Physics feature") may be considered features that are local to specific points within a given patient's geometric model. In addition, features (i) thru (vi) may be considered variables within the function of boundary conditions, f(BCs), while features (vii) thru (xv) may be considered variables within the function of geometry, g(areaReductions), on that page. It will be appreciated that any combination of those features, modified by any desired weighting scheme, may be incorporated into a machine learning algorithm executed according to the disclosed embodiments.

In another embodiment, systems and methods are described to obtain estimates of physiologic metrics, such as ischemia, blood flow, or FFR from patient-specific anatomy and characteristics. The system may consist of a computer and software either on-site at a hospital or off-site that physicians load or transfer patient-specific data to. The anatomic data may consist of imaging data (ie CT) or measurements and anatomic representation already obtained from imaging data (quantitative angiography, vessel segmentations from third party software, vascular diameters, etc). Other patient characteristics may consist of heart rate, blood pressure, demographics such as age or sex, medication, disease states including diabetes and hypertension, prior MI, etc.

After relevant data is received by the system, it may be processed by software automation, the physician using the system, a third-party technician or analyst using the system, or any combination. The data may be processed using algorithms relating the patient's anatomy and characteristics to functional estimates of ischemia and blood flow. The algorithms may employ empirically derived models, machine learning, or analytical models relating blood flow to anatomy. Estimates of ischemia (blood flow, FFR, etc) may be generated for a specific location in a vessel, as an overall estimate for the vessel, or for an entire system of vessels such as the coronary arteries. A numeric output, such as an FFR value, may be generated or simple positive/negative/inconclusive indications based on clinical metrics may be provided (ie FFR> or <0.80). Along with the output, a confidence may be provided. Results of the analysis may be displayed or stored in a variety of media, including images, renderings, tables of values, or reports and may be transferred back to the physician through the system or through other electronic or physical delivery methods.

In one embodiment, the algorithm to estimate FFR from patient anatomy consists of deriving an analytical model based on fundamentals of physiology and physics, for example analytical fluid dynamics equations and morphometry scaling laws. Information about the following coronary anatomy, including but not limited to the following features derived from imaging data (ie CT), serves as an input:

Vessel sizes
Vessel size at ostium
Vessel size at distal branches
Reference and minimum vessel size at plaque
Distance from ostium to plaque
Length of plaque and length of minimum vessel size
Myocardial volume
Branches proximal/distal to measurement location
Branches proximal/distal to plaque
Measurement location Using some or all of the information above, a network of flow resistance may be created. Pressure drop may be estimated by relating the amount of blood flow to the resistance to blood flow using any of a variety of analytical models, such as Poiseuille's equation, energy loss models, etc. As an example embodiment:

$$FFR=(P-\Delta P)/P$$

where P is the aortic pressure and $\Delta P$ is the change in pressure from the aorta to the location of interest.

$$\Delta P = QR,$$

where Q is flow rate, and R is resistance

The flow rate may be estimated by morphometry relations, such as $Q \propto M^k$ where M is the myocardial volume and k is an exponent, often approximately 0.75. Individual vessel flow rates may scale based on the morphometry relationship of $Q \propto D^k$ where D is the diameter of the vessel and k is an exponent, often between 2 and 3.

In an example embodiment, the resistance through a vessel may be estimated by Poiseuille's equation:

$$R \propto \mu L/D^4$$

where u is viscosity, L is length, and D is diameter

Downstream, or microvascular resistances may be estimated through morphometric tree generation or other methods described in Ser. No. 13/014,809 and U.S. Pat. No. 8,157,742. FFR can be estimated by relating all the resistance and flow estimates in a network representing the distribution of vessels in the coronary circulation, and pressure can be solved.

In another embodiment, regression or machine learning may be employed to train the algorithm using the features previously mentioned, formulations of resistances and flows, and additional anatomic and patient characteristics, including but not limited to:

Age, sex, and other demographics
Heart rate, blood pressure, and other physiologic measures Disease state, such as hypertension, diabetes, previous cardiac events Vessel dominance Plaque type Plaque shape Prior simulation results, such as full 3D simulations of FFR A library or database of anatomic and patient characteristics along with FFR, ischemia test results, previous simulation results, imaging data, or other metrics may be compiled. For every point of interest where an FFR estimation is required, a set of features may be generated. A regression or machine learning technique, such as linear regression or decision trees, may be used to define which features have the largest impact on estimating FFR and to create an algorithm that weights the various features. Example embodiments may estimate FFR numerically, classify a vessel as ischemia positive or negative, or classify a patient as ischemia positive or negative.

Once an algorithm is created, it may be executed on new data provided by the physician to the system. As previously described, a number of methods may be used to generate the anatomic information required, and once obtained, the features defined, algorithm performed, and results reported. Along with numerical or classification results, a confidence from the machine learning algorithm may be provided. One example embodiment is to report that a particular vessel in a patient has a specific percent confidence of being positive or negative for ischemia, ie Left anterior descending artery is positive with 85% confidence. Over time, the algorithm may be refined or updated as additional patient data is added to the library or database.

One additional embodiment is to derive any of the previously mentioned parameters, physiologic, or physical estimations empirically. Coupled with machine learning or analytic techniques, empirical studies of flow and pressure across various geometries may be utilized to inform the algorithms.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for personalized non-invasive assessment of artery stenosis for a patient, comprising:
    receiving medical image data of at least a part of the patient's vascular system including one or more arteries of the patient;
    extracting patient-specific arterial geometry of the patient from the received medical image data;
    extracting features from the patient-specific arterial geometry of the patient, the extracted features corresponding to features of a trained machine-learning based model for predicting physiologic values based on learned associations between the physiologic values and the extracted features; and
    automatically computing one or more index values of the physiologic values for one or more locations of interest in the patient-specific arterial geometry based on the extracted features using the trained machine-learning based model trained based on features extracted from one or both of anatomical features extracted from individuals other than the patient and synthetically generated arterial geometries, based on the learned associations between the physiologic values and the extracted features.

2. The method of claim 1, further comprising:
    receiving at least one of non-invasive physiological measurements of the patient or demographic data of the patient,
    wherein computing the one or more index values is further based on features corresponding to the at least one of the non-invasive physiological measurements of the patient or the demographic data of the patient.

3. The method of claim 1, further comprising
    receiving one or more biomarkers of the patient,
    wherein computing the one or more index values is further based on features corresponding to the one or more biomarkers of the patient.

4. The method of claim 1, wherein the physiologic values are physiologic blood pressure values, and the trained machine-learning based model is trained based on one or more patient-specific models of blood flow circulation.

5. The method of claim 1, wherein extracting features from the patient-specific arterial geometry of the patient further comprises:
    extracting a plurality of geometric measurements for one or more artery stenosis regions in the patient-specific arterial geometry of the patient.

6. The method of claim 1, wherein the one or more locations of interest correspond to one or more artery stenosis locations.

7. The method of claim 1, wherein computing the one or more index values for one or more locations of interest in the patient-specific arterial geometry is in response to a user input identifying the one or more locations of interest.

8. The method of claim 1, wherein the physiologic values are physiologic blood pressure values and the one or more index values are one or more fractional flow reserve (FFR) values.

9. The method of claim 1, wherein computing the one or more index values comprises:
    computing a plurality of hemodynamic indices of the physiologic values for each of the one or more locations of interest in the patient-specific arterial geometry based on the extracted features using a respective one of a plurality of trained machine-learning based models trained based on the features extracted from the one or both of anatomical features extracted from individuals other the patient and/or synthetically generated arterial geometries, based on the learned associations between physiologic values and the extracted features.

10. The method of claim 1, further comprising: displaying a visualization of the patient-specific arterial geometry color coded based on the one or more index values computed for the one or more locations of interest in the patient-specific arterial geometry.

11. A system for personalized non-invasive assessment of artery stenosis for a patient, comprising:
    at least one data storage device storing instructions for personalized non-invasive assessment of artery stenosis for a patient in an electronic storage medium; and
    at least one processor configured to execute the instructions to perform operations comprising:
        receiving medical image data of at least a part of the patient's vascular system including one or more arteries of the patient;
        extracting patient-specific arterial geometry of the patient from the received medical image data;

extracting features from the patient-specific arterial geometry of the patient, the extracted features corresponding to features of a trained machine-learning based model for predicting physiologic values based on learned associations between the physiologic values and the extracted features; and automatically computing one or more index values of the physiologic values for one or more locations of interest in the patient-specific arterial geometry based on the extracted features using the trained machine-learning based model trained based on features extracted from one or both of anatomical features extracted from individuals other than the patient and synthetically generated arterial geometries, based on the learned associations between the physiologic values and the extracted features.

12. The system of claim 11, the operations further comprising:

receiving at least one of non-invasive physiological measurements of the patient or demographic data of the patient, wherein computing the one or more index values is further based on based on features corresponding to at least one of the non-invasive physiological measurements of the patient or the demographic data of the patient using the trained machine-learning based model.

13. The system of claim 11, the operations further comprising:

receiving one or more biomarkers of the patient, wherein computing the one or more index values is further based on features corresponding to one or more biomarkers of the patient using the trained machine-learning based model.

14. The system of claim 11, wherein the physiologic values are physiologic blood pressure values, and the trained machine-learning based model is trained based on one or more patient-specific multi-scale models of blood flow circulation.

15. The system of claim 11, wherein the physiologic values are physiologic blood pressure values, the one or more index values are one or more fractional flow reserve (FFR) values.

16. The system of claim 11, wherein computing the one or more index values comprises:

computing a plurality of hemodynamic indices of the physiologic values for each of the one or more locations of interest in the patient-specific arterial geometry based on the extracted features using a respective one of a plurality of trained machine-learning based models trained based on the features extracted from the one or both of anatomical features extracted from individuals other the patient and/or synthetically generated arterial geometries, based on the learned associations between physiologic values and the extracted features.

17. The system of claim 11, further comprising: displaying a visualization of the patient-specific arterial geometry color coded based on the one or more index values computed for the one or more locations of interest in the patient-specific arterial geometry.

18. A non-transitory computer readable medium, for personalized non-invasive assessment of artery stenosis for a patient, storing operations comprising:

receiving medical image data of at least a part of the patient's vascular system including one or more arteries of the patient;

extracting patient-specific arterial geometry of the patient from the received medical image data;

extracting features from the patient-specific arterial geometry of the patient, the extracted features corresponding to features of a trained machine-learning based model for predicting physiologic values based on learned associations between the physiologic values and the extracted features; and automatically computing one or more index values of the physiologic values for one or more locations of interest in the patient-specific arterial geometry based on the extracted features using the trained machine-learning based model trained based on features extracted from one or both of anatomical features extracted from individuals other than the patient and synthetically generated arterial geometries, based on the learned associations between the physiologic values and the extracted features.

19. The computer-readable medium of claim 18, the operations further comprising:

receiving at least one of non-invasive physiological measurements of the patient or demographic data of the patient, wherein computing the one or more index values is further based on based on features corresponding to at least one of the non-invasive physiological measurements of the patient or the demographic data of the patient using the trained machine-learning based model.

20. The computer-readable medium of claim 18, the operations further comprising:

receiving one or more biomarkers of the patient, wherein computing the one or more index values is further based on features corresponding to one or more biomarkers of the patient using the trained machine-learning based model.

* * * * *